US 11,420,023 B2

(12) United States Patent
Andino et al.

(10) Patent No.: US 11,420,023 B2
(45) Date of Patent: Aug. 23, 2022

(54) STABILIZING DEVICE HAVING A SNAP CLAMP

(71) Applicant: Venetec International, Inc., Covington, GA (US)

(72) Inventors: Rafael V. Andino, Grayson, GA (US); Christopher J. Brooks, Huntington, NY (US)

(73) Assignee: Venetec International, Inc., Covington, GA (US)

( * ) Notice: Subject to any disclaimer, the term of this patent is extended or adjusted under 35 U.S.C. 154(b) by 373 days.

(21) Appl. No.: 16/589,121

(22) Filed: Sep. 30, 2019

(65) Prior Publication Data
US 2020/0030578 A1    Jan. 30, 2020

Related U.S. Application Data

(63) Continuation of application No. 15/637,909, filed on Jun. 29, 2017, now Pat. No. 10,426,928, which is a
(Continued)

(51) Int. Cl.
*A61M 25/02*    (2006.01)
*A61M 5/14*    (2006.01)

(52) U.S. Cl.
CPC .......... *A61M 25/02* (2013.01); *A61M 5/1418* (2013.01); *A61M 2005/1416* (2013.01);
(Continued)

(58) Field of Classification Search
CPC ................ A61M 25/02; A61M 5/1418; A61M 2005/1416; A61M 2025/024; A61M 2025/0266; A61M 2025/028
(Continued)

(56) References Cited

U.S. PATENT DOCUMENTS 2,402,306 A    6/1946    Turkel
2,525,398 A    10/1950    Collins
(Continued)

FOREIGN PATENT DOCUMENTS

CA    1311977 C    12/1992
CA    1318824 C    6/1993
(Continued)

OTHER PUBLICATIONS

ARROW International, Inc. Multiple-Lumen Central Venous Catheterization Product with ARROWgard™ Antiseptic Surface, 6 pgs., K-24703-1008 (Apr. 1994).
(Continued)

*Primary Examiner* — Phillip A Gray
(74) *Attorney, Agent, or Firm* — Rutan & Tucker LLP (57) ABSTRACT

A retainer includes a first arcuate wall and a second arcuate wall that together define a channel designed to receive a medical article. The retainer has an open configuration wherein a first end of the first arcuate wall is spaced away from a first end of the second arcuate wall, and a closed configuration wherein the first end of the first arcuate wall is adjacent the first end of the second arcuate wall. A second end of the first arcuate wall opposite the first end of the arcuate wall may be spaced away from the base in the open configuration and pressed against the base in the closed configuration. The retainer also may include a first support and a second support fixed to the base, and a first and second flexible coupling connecting the first and second supports to the first and second arcuate walls.

15 Claims, 7 Drawing Sheets

Related U.S. Application Data continuation of application No. 13/498,118, filed as application No. PCT/US2010/051706 on Oct. 6, 2010, now Pat. No. 9,694,130.

(60) Provisional application No. 61/249,212, filed on Oct. 6, 2009.

(52) U.S. Cl.
CPC . *A61M 2025/024* (2013.01); *A61M 2025/028* (2013.01); *A61M 2025/0266* (2013.01); *A61M 2209/088* (2013.01)

(58) Field of Classification Search
USPC .......................................................... 604/180
See application file for complete search history.

(56) References Cited

U.S. PATENT DOCUMENTS

| | | |
|---|---|---|
| 2,533,961 A | 12/1950 | Rousseau et al. |
| 2,707,953 A | 5/1955 | Ryan |
| 3,046,984 A | 7/1962 | Eby |
| 3,059,645 A | 10/1962 | Hasbrouck et al. |
| 3,064,648 A | 11/1962 | Bujan |
| 3,167,072 A | 1/1965 | Stone et al. |
| 3,194,235 A | 7/1965 | Cooke |
| 3,245,567 A | 4/1966 | Knight |
| 3,288,137 A | 11/1966 | Lund |
| 3,394,954 A | 7/1968 | Sams |
| 3,482,569 A | 12/1969 | Raaelli, Sr. |
| 3,529,597 A | 9/1970 | Fuzak |
| 3,589,361 A | 6/1971 | Loper et al. |
| 3,602,227 A | 8/1971 | Andrew |
| 3,613,663 A | 10/1971 | Johnson |
| 3,630,195 A | 12/1971 | Santomieri |
| 3,677,250 A | 7/1972 | Thomas |
| 3,686,896 A | 8/1972 | Rutter |
| 3,766,915 A | 10/1973 | Rychlik |
| 3,782,383 A | 1/1974 | Thompson et al. |
| 3,812,851 A | 5/1974 | Rodriguez |
| 3,826,254 A | 7/1974 | Mellor |
| 3,834,380 A | 9/1974 | Boyd |
| 3,856,020 A | 12/1974 | Kovac |
| 3,863,527 A | 2/1975 | Beming |
| 3,863,631 A | 2/1975 | Baldwin |
| 3,900,026 A | 8/1975 | Wagner |
| 3,901,226 A | 8/1975 | Scardenzan |
| 3,906,946 A | 9/1975 | Nordstrom |
| 3,920,001 A | 11/1975 | Edwards |
| 3,942,228 A | 3/1976 | Buckman et al. |
| 3,973,565 A | 8/1976 | Steer |
| 3,993,081 A | 11/1976 | Cussell |
| 4,004,586 A | 1/1977 | Christensen et al. |
| D243,477 S | 2/1977 | Cutruzzula et al. |
| 4,020,835 A | 5/1977 | Nordstrom et al. |
| 4,037,599 A | 7/1977 | Raulerson |
| 4,057,066 A | 11/1977 | Taylor |
| 4,059,105 A | 11/1977 | Cutruzzula et al. |
| 4,079,738 A | 3/1978 | Dunn et al. |
| 4,082,094 A | 4/1978 | Dailey |
| 4,114,618 A | 9/1978 | Margas |
| 4,116,196 A | 9/1978 | Kaplan et al. |
| 4,123,091 A | 10/1978 | Cosentino et al. |
| 4,129,128 A | 12/1978 | McFarlane |
| 4,133,312 A | 1/1979 | Burd |
| 4,142,527 A | 3/1979 | Garcia |
| 4,161,177 A | 7/1979 | Fuchs |
| 4,165,748 A | 8/1979 | Johnson |
| D252,822 S | 9/1979 | McFarlane |
| 4,170,993 A | 10/1979 | Alvarez |
| 4,170,995 A | 10/1979 | Levine et al. |
| 4,182,455 A | 1/1980 | Rawin |
| 4,193,174 A | 3/1980 | Stephens |
| 4,194,504 A | 3/1980 | Harms et al. |
| D256,162 S | 7/1980 | Haerr et al. |
| 4,224,937 A | 9/1980 | Gordon |
| 4,230,109 A | 10/1980 | Geiss |
| 4,248,229 A | 2/1981 | Miller |
| 4,250,880 A | 2/1981 | Gordon |
| 4,275,721 A | 6/1981 | Olson |
| 4,284,076 A | 8/1981 | Hall |
| 4,314,568 A | 2/1982 | Loving |
| 4,316,461 A | 2/1982 | Marais et al. |
| 4,324,236 A | 4/1982 | Gordon et al. |
| 4,326,519 A | 4/1982 | D'Alo et al. |
| 4,333,468 A | 6/1982 | Geist |
| 4,356,599 A | 11/1982 | Larson et al. |
| 4,362,156 A | 12/1982 | Feller, Jr. et al. |
| 4,389,754 A | 6/1983 | Sohma |
| 4,392,853 A | 7/1983 | Muto |
| 4,397,647 A | 8/1983 | Gordon |
| 4,398,757 A | 8/1983 | Floyd et al. |
| 4,405,163 A | 9/1983 | Voges et al. |
| 4,405,312 A | 9/1983 | Gross et al. |
| 4,435,174 A | 3/1984 | Redmond et al. |
| 4,435,175 A | 3/1984 | Friden |
| 4,439,193 A | 3/1984 | Larkin |
| D273,993 S | 5/1984 | Schulte et al. |
| 4,449,975 A | 5/1984 | Perry |
| 4,453,933 A | 6/1984 | Speaker |
| 4,470,410 A | 9/1984 | Elliott |
| 4,474,559 A | 10/1984 | Steiger |
| 4,480,639 A | 11/1984 | Peterson et al. |
| 4,484,913 A | 11/1984 | Swauger |
| 4,500,338 A | 2/1985 | Young et al. |
| 4,516,968 A | 5/1985 | Marshall et al. |
| 4,517,971 A | 5/1985 | Sorbonne |
| 4,533,349 A | 8/1985 | Bark |
| 4,561,857 A | 12/1985 | Sacks |
| 4,563,177 A | 1/1986 | Kamen |
| 4,583,976 A | 4/1986 | Ferguson |
| 4,585,435 A | 4/1986 | Vaillancourt |
| 4,585,444 A | 4/1986 | Harris |
| 4,621,029 A | 11/1986 | Kawaguchi |
| 4,623,102 A | 11/1986 | Hough, Jr. |
| 4,627,842 A | 12/1986 | Katz |
| 4,631,056 A | 12/1986 | Dye |
| 4,632,670 A | 12/1986 | Mueller, Jr. |
| 4,633,863 A | 1/1987 | Filips et al. |
| 4,636,552 A | 1/1987 | Gay et al. |
| 4,645,492 A | 2/1987 | Weeks |
| 4,650,473 A | 3/1987 | Bartholomew et al. |
| 4,659,329 A | 4/1987 | Annis |
| 4,660,555 A | 4/1987 | Payton |
| 4,666,434 A | 5/1987 | Kaufman |
| 4,669,458 A | 6/1987 | Abraham et al. |
| 4,683,882 A | 8/1987 | Laird |
| 4,693,710 A | 9/1987 | McCool |
| 4,699,616 A | 10/1987 | Nowak et al. |
| 4,711,636 A | 12/1987 | Bierman |
| 4,723,948 A | 2/1988 | Clark et al. |
| 4,733,666 A | 3/1988 | Mercer, Jr. |
| 4,737,143 A | 4/1988 | Russell |
| 4,742,824 A | 5/1988 | Payton et al. |
| 4,743,231 A | 5/1988 | Kay et al. |
| 4,752,292 A | 6/1988 | Lopez et al. |
| 4,775,121 A | 10/1988 | Carty |
| 4,792,163 A | 12/1988 | Kulle |
| 4,795,429 A | 1/1989 | Feldstein |
| 4,808,162 A | 2/1989 | Oliver |
| 4,822,342 A | 4/1989 | Brawner |
| 4,826,486 A | 5/1989 | Palsrok et al. |
| 4,832,019 A | 5/1989 | Weinstein et al. |
| 4,834,702 A | 5/1989 | Rocco |
| 4,834,716 A | 5/1989 | Ogle, II |
| 4,838,858 A | 6/1989 | Wortham et al. |
| D302,304 S | 7/1989 | Kulle et al. |
| 4,846,807 A | 7/1989 | Safadago |
| 4,852,844 A | 8/1989 | Villaveces |
| 4,857,058 A | 8/1989 | Payton Hugh W. |
| 4,863,432 A | 9/1989 | Kvalo |
| 4,878,897 A | 11/1989 | Katzin |
| 4,880,412 A | 11/1989 | Weiss |

(56) References Cited

U.S. PATENT DOCUMENTS

| | | |
|---|---|---|
| 4,897,082 A | 1/1990 | Erskine |
| 4,898,587 A | 2/1990 | Mera |
| 4,919,654 A | 4/1990 | Kalt |
| 4,921,199 A | 5/1990 | Villaveces |
| 4,932,943 A | 6/1990 | Nowak |
| 4,934,375 A | 6/1990 | Cole et al. |
| 4,941,882 A | 7/1990 | Ward et al. |
| 4,955,864 A | 9/1990 | Hajduch |
| 4,961,505 A | 10/1990 | Moeller |
| 4,966,582 A | 10/1990 | Sit et al. |
| 4,976,700 A | 12/1990 | Tollini |
| 4,981,469 A | 1/1991 | Whitehouse et al. |
| 4,981,475 A | 1/1991 | Haindl |
| 4,986,815 A | 1/1991 | Schneider |
| 4,997,421 A | 3/1991 | Palsrok et al. |
| 5,024,665 A | 6/1991 | Kaufman |
| 5,037,397 A | 8/1991 | Kalt et al. |
| 5,037,398 A | 8/1991 | Buchanan |
| 5,037,405 A | 8/1991 | Crosby |
| 5,069,206 A | 12/1991 | Crosbie |
| 5,073,170 A | 12/1991 | Schneider |
| 5,074,847 A | 12/1991 | Greenwell et al. |
| D323,390 S | 1/1992 | Paine et al. |
| 5,084,026 A | 1/1992 | Shapiro |
| 5,098,048 A | 3/1992 | Chen |
| 5,098,399 A | 3/1992 | Tollini |
| 5,105,807 A | 4/1992 | Kahn et al. |
| 5,112,313 A | 5/1992 | Sallee |
| 5,116,324 A | 5/1992 | Brierley et al. |
| 5,120,320 A | 6/1992 | Fayngold |
| 5,135,506 A | 8/1992 | Gentelia et al. |
| 5,137,519 A | 8/1992 | Littrell et al. |
| 5,147,322 A | 9/1992 | Bowen et al. |
| 5,156,641 A | 10/1992 | White |
| 5,192,273 A | 3/1993 | Bierman |
| 5,192,274 A | 3/1993 | Bierman |
| 5,195,981 A | 3/1993 | Johnson |
| 5,215,532 A | 6/1993 | Atkinson |
| 5,226,892 A | 7/1993 | Boswell |
| 5,236,421 A | 8/1993 | Becher |
| 5,238,010 A | 8/1993 | Grabenkort et al. |
| 5,248,306 A | 9/1993 | Clark et al. |
| 5,263,943 A | 11/1993 | Vanderbrook |
| 5,266,401 A | 11/1993 | Tollini |
| 5,267,967 A | 12/1993 | Schneider |
| 5,279,578 A | 1/1994 | Cooke |
| 5,290,248 A | 3/1994 | Bierman et al. |
| 5,292,013 A | 3/1994 | Earl |
| 5,292,312 A | 3/1994 | Delk et al. |
| 5,304,146 A | 4/1994 | Johnson et al. |
| 5,306,243 A | 4/1994 | Bonaldo |
| D347,060 S | 5/1994 | Bierman |
| 5,308,337 A | 5/1994 | Bingisser |
| 5,314,411 A | 5/1994 | Bierman et al. |
| 5,322,097 A | 6/1994 | Wright |
| 5,328,487 A | 7/1994 | Starchevich |
| 5,334,186 A | 8/1994 | Alexander |
| 5,336,195 A | 8/1994 | Daneshvar |
| 5,338,308 A | 8/1994 | Wilk |
| 5,342,317 A | 8/1994 | Claywell |
| 5,344,406 A | 9/1994 | Spooner |
| 5,344,414 A | 9/1994 | Lopez et al. |
| 5,352,211 A | 10/1994 | Merskelly |
| 5,354,282 A | 10/1994 | Bierman |
| 5,356,379 A | 10/1994 | Vaillancourt |
| 5,356,391 A | 10/1994 | Stewart |
| 5,370,627 A | 12/1994 | Conway |
| 5,372,589 A | 12/1994 | Davis |
| 5,380,293 A | 1/1995 | Grant |
| 5,380,294 A | 1/1995 | Persson |
| 5,380,301 A | 1/1995 | Prichard et al. |
| 5,380,395 A | 1/1995 | Uchida |
| 5,382,239 A | 1/1995 | Orr et al. |
| 5,382,240 A | 1/1995 | Lam |
| 5,389,082 A | 2/1995 | Bauges et al. |
| 5,395,344 A | 3/1995 | Beisang, III et al. |
| 5,402,776 A | 4/1995 | Islava |
| 5,403,285 A | 4/1995 | Roberts |
| 5,413,120 A | 5/1995 | Grant |
| 5,413,562 A | 5/1995 | Swauger |
| D359,120 S | 6/1995 | Sallee et al. |
| 5,443,460 A | 8/1995 | Miklusek |
| 5,449,344 A | 9/1995 | Taylor et al. |
| 5,456,671 A | 10/1995 | Bierman |
| 5,468,231 A | 11/1995 | Newman et al. |
| 5,470,321 A | 11/1995 | Forster et al. |
| D364,922 S | 12/1995 | Bierman |
| 5,484,420 A | 1/1996 | Russo |
| 5,484,425 A | 1/1996 | Fischell et al. |
| 5,494,245 A | 2/1996 | Suzuki et al. |
| 5,496,282 A | 3/1996 | Militzer et al. |
| 5,496,283 A | 3/1996 | Alexander |
| 5,498,241 A | 3/1996 | Fabozzi |
| 5,499,976 A | 3/1996 | Dalton |
| 5,507,535 A | 4/1996 | McKamey et al. |
| 5,520,656 A | 5/1996 | Byrd |
| 5,522,803 A | 6/1996 | Teissen-Simony |
| 5,527,293 A | 6/1996 | Zamierowski |
| 5,531,695 A | 7/1996 | Swisher |
| 5,539,020 A | 7/1996 | Bracken et al. |
| 5,549,567 A | 8/1996 | Wolman |
| 5,551,421 A | 9/1996 | Noureldin et al. |
| D375,355 S | 11/1996 | Bierman |
| 5,577,516 A | 11/1996 | Schaeffer |
| 5,578,013 A | 11/1996 | Bierman |
| 5,593,395 A | 1/1997 | Martz |
| 5,605,546 A | 2/1997 | Wolzinger et al. |
| 5,620,427 A | 4/1997 | Werschmidt et al. |
| 5,626,565 A | 5/1997 | Landis et al. |
| 5,637,098 A | 6/1997 | Bierman |
| 5,643,217 A | 7/1997 | Dobkin |
| 5,664,581 A | 9/1997 | Ashley |
| 5,681,290 A | 10/1997 | Alexander |
| 5,685,859 A | 11/1997 | Komerup |
| 5,686,096 A | 11/1997 | Khan et al. |
| 5,690,616 A | 11/1997 | Mogg |
| 5,690,617 A | 11/1997 | Wright |
| 5,693,032 A | 12/1997 | Bierman |
| 5,702,371 A | 12/1997 | Bierman |
| D389,911 S | 1/1998 | Bierman |
| 5,722,959 A | 3/1998 | Bierman |
| 5,728,053 A | 3/1998 | Calvert |
| 5,755,225 A * | 5/1998 | Hutson ............. A61M 16/0488 128/207.14 |
| 5,776,106 A | 7/1998 | Matyas |
| 5,800,402 A | 9/1998 | Bierman |
| 5,800,410 A | 9/1998 | Gawreluk |
| 5,810,781 A | 9/1998 | Bierman |
| D399,954 S | 10/1998 | Bierman |
| 5,827,230 A | 10/1998 | Bierman |
| 5,827,239 A | 10/1998 | Dillon et al. |
| 5,833,666 A | 11/1998 | Davis et al. |
| 5,833,667 A | 11/1998 | Bierman |
| 5,846,255 A | 12/1998 | Casey |
| 5,855,591 A | 1/1999 | Bierman |
| 5,885,251 A | 3/1999 | Luther |
| 5,885,254 A | 3/1999 | Matyas |
| 5,897,519 A | 4/1999 | Shesol et al. |
| 5,911,707 A | 6/1999 | Wolvek et al. |
| 5,916,199 A | 6/1999 | Miles |
| 5,922,470 A | 7/1999 | Bracken et al. |
| 5,944,696 A | 8/1999 | Bayless et al. |
| 5,947,931 A | 9/1999 | Bierman |
| 6,015,119 A | 1/2000 | Starchevich |
| 6,050,934 A | 4/2000 | Mikhail et al. |
| 6,054,523 A | 4/2000 | Braun et al. |
| D425,619 S | 5/2000 | Bierman |
| 6,058,574 A | 5/2000 | Facey et al. |
| 6,067,985 A | 5/2000 | Islava |
| 6,099,509 A | 8/2000 | Brown, Jr. et al. |
| 6,113,577 A | 9/2000 | Hakky et al. |
| 6,131,575 A | 10/2000 | Lenker et al. |
| 6,132,398 A | 10/2000 | Bierman |
| 6,132,399 A | 10/2000 | Shultz |

(56) References Cited

U.S. PATENT DOCUMENTS

| | | |
|---|---|---|
| D433,503 S | 11/2000 | Powers et al. |
| 6,206,897 B1 | 3/2001 | Jamiolkowski et al. |
| 6,213,979 B1 | 4/2001 | Bierman |
| 6,213,996 B1 | 4/2001 | Jepson et al. |
| 6,216,885 B1 | 4/2001 | Guillaume |
| 6,224,571 B1 | 5/2001 | Bierman |
| 6,228,064 B1 | 5/2001 | Abita et al. |
| 6,231,547 B1 | 5/2001 | O'Hara |
| 6,231,548 B1 | 5/2001 | Bassett |
| 6,234,465 B1 | 5/2001 | Sutton, Jr. |
| 6,258,066 B1 | 7/2001 | Urich |
| 6,273,873 B1 | 8/2001 | Fleischer |
| 6,283,945 B1 | 9/2001 | Bierman |
| 6,287,281 B1 | 9/2001 | Nishtala et al. |
| 6,290,676 B1 | 9/2001 | Bierman |
| 6,332,874 B1 | 12/2001 | Eliasen et al. |
| 6,361,523 B1 | 3/2002 | Bierman |
| 6,375,639 B1 | 4/2002 | Duplessie et al. |
| 6,387,075 B1 | 5/2002 | Stiviand et al. |
| 6,387,076 B1 | 5/2002 | Landuyt |
| 6,413,240 B1 | 7/2002 | Bierman et al. |
| 6,428,515 B1 | 8/2002 | Bierman et al. |
| 6,428,516 B1 | 8/2002 | Bierman |
| 6,436,073 B1 | 8/2002 | Von Teichert |
| 6,447,485 B2 | 9/2002 | Bierman |
| 6,447,486 B1 | 9/2002 | Tollini |
| 6,471,676 B1 | 10/2002 | DeLegge et al. |
| 6,482,183 B1 | 11/2002 | Pausch et al. |
| 6,488,664 B1 | 12/2002 | Solomon et al. |
| 6,491,664 B2 | 12/2002 | Bierman |
| 6,500,154 B1 | 12/2002 | Hakky et al. |
| D469,530 S | 1/2003 | Gomez |
| 6,517,522 B1 | 2/2003 | Bell et al. |
| 6,551,285 B1 | 4/2003 | Bierman |
| 6,572,588 B1 | 6/2003 | Bierman et al. |
| 6,582,403 B1 | 6/2003 | Bierman et al. |
| 6,596,402 B2 | 7/2003 | Soerens et al. |
| 6,616,635 B1 | 9/2003 | Bell et al. |
| 6,626,890 B2 | 9/2003 | Nguyen et al. |
| 6,652,487 B1 | 11/2003 | Cook |
| 6,663,600 B2 | 12/2003 | Bierman et al. |
| 6,673,046 B2 | 1/2004 | Bierman et al. |
| 6,689,104 B2 | 2/2004 | Bierman |
| 6,703,120 B1 | 3/2004 | Ko et al. |
| 6,770,055 B2 | 8/2004 | Bierman et al. |
| 6,786,892 B2 | 9/2004 | Bierman |
| 6,809,230 B2 | 10/2004 | Hancock et al. |
| 6,827,705 B2 | 12/2004 | Bierman |
| 6,827,706 B2 | 12/2004 | Tollini |
| 6,827,707 B2 | 12/2004 | Wright et al. |
| 6,834,652 B2 | 12/2004 | Altman |
| 6,837,875 B1 | 1/2005 | Bierman |
| 6,866,652 B2 | 3/2005 | Bierman |
| 6,951,550 B2 | 10/2005 | Bierman |
| 6,972,003 B2 | 12/2005 | Bierman et al. |
| 6,979,320 B2 | 12/2005 | Bierman |
| 6,981,969 B2 | 1/2006 | Chavez et al. |
| 7,014,627 B2 | 3/2006 | Bierman |
| 7,018,362 B2 | 3/2006 | Bierman et al. |
| 7,070,580 B2 | 7/2006 | Nielsen |
| 7,090,660 B2 | 8/2006 | Roberts et al. |
| 7,115,321 B2 | 10/2006 | Soerens et al. |
| 7,153,291 B2 | 12/2006 | Bierman |
| 7,201,739 B2 | 4/2007 | Walborn |
| 7,214,215 B2 | 5/2007 | Heinzerling et al. |
| 7,223,256 B2 | 5/2007 | Bierman |
| 7,250,880 B2 | 7/2007 | Hurrell et al. |
| 7,354,421 B2 | 4/2008 | Bierman |
| 7,413,561 B2 | 8/2008 | Raulerson et al. |
| 7,491,190 B2 | 2/2009 | Bierman et al. |
| 7,520,870 B2 | 4/2009 | Bierman |
| 7,524,307 B2 | 4/2009 | Davis et al. |
| 7,566,325 B2 | 7/2009 | Lim et al. |
| 7,637,894 B2 | 12/2009 | Fleischer |
| 7,651,479 B2 | 1/2010 | Bierman |
| 7,744,572 B2 | 6/2010 | Bierman |
| 7,776,017 B2 | 8/2010 | Ponzi et al. |
| 7,799,001 B2 | 9/2010 | Bierman |
| 7,887,515 B2 | 2/2011 | Bierman |
| 7,967,792 B2 | 6/2011 | Bierman |
| 7,974,681 B2 | 7/2011 | Wallace et al. |
| 8,100,862 B2 | 1/2012 | Bierman |
| 8,105,290 B2 | 1/2012 | Wright et al. |
| 8,900,196 B2 | 12/2014 | Andino |
| 9,604,034 B2 | 3/2017 | Andino |
| 9,694,130 B2 | 7/2017 | Andino et al. |
| 10,426,928 B2 | 10/2019 | Andino et al. |
| 2001/0011164 A1 | 8/2001 | Bierman |
| 2002/0133121 A1 | 9/2002 | Bierman |
| 2002/0161332 A1 | 10/2002 | Ramey |
| 2002/0165494 A1 | 11/2002 | Bierman et al. |
| 2002/0188255 A1 | 12/2002 | Bierman et al. |
| 2003/0055382 A1 | 3/2003 | Schaeffer |
| 2004/0111067 A1 | 6/2004 | Kirchhofer |
| 2004/0170089 A1 | 9/2004 | Rund |
| 2004/0204685 A1 | 10/2004 | Wright et al. |
| 2004/0240324 A1 | 12/2004 | Isbitsky et al. |
| 2005/0038453 A1 | 2/2005 | Raulerson |
| 2005/0075610 A1 | 4/2005 | Bierman |
| 2005/0107738 A1 | 5/2005 | Slater et al. |
| 2005/0192539 A1 | 9/2005 | Bierman et al. |
| 2005/0215953 A1 | 9/2005 | Rossen |
| 2005/0251157 A1 | 11/2005 | Saadat et al. |
| 2005/0282977 A1 | 12/2005 | Stempel et al. |
| 2006/0025723 A1 | 2/2006 | Ballarini |
| 2006/0052755 A1 | 3/2006 | Lim et al. |
| 2006/0058789 A1 | 3/2006 | Kim et al. |
| 2006/0089600 A1 | 4/2006 | Bierman et al. |
| 2006/0094985 A1 | 5/2006 | Aceti et al. |
| 2006/0135944 A1 | 6/2006 | Bierman |
| 2006/0161087 A1 | 7/2006 | Carter et al. |
| 2006/0184129 A1 | 8/2006 | Bierman |
| 2006/0217669 A1 | 9/2006 | Botha |
| 2006/0247574 A1 | 11/2006 | Maule et al. |
| 2006/0247577 A1 | 11/2006 | Wright |
| 2006/0247661 A1 | 11/2006 | Richards et al. |
| 2006/0270995 A1 | 11/2006 | Bierman |
| 2006/0289011 A1 | 12/2006 | Helsel |
| 2007/0032561 A1 | 2/2007 | Lin et al. |
| 2007/0043385 A1 | 2/2007 | Nobles et al. |
| 2007/0060890 A1 | 3/2007 | Cuppy |
| 2007/0149930 A1 | 6/2007 | Bierman |
| 2007/0173768 A2 | 7/2007 | Bierman |
| 2007/0249980 A1 | 10/2007 | Carrez et al. |
| 2007/0276332 A1 | 11/2007 | Bierman |
| 2007/0276333 A1 | 11/2007 | Bierman |
| 2008/0027392 A1 | 1/2008 | Bierman |
| 2008/0249476 A1 | 10/2008 | Bierman et al. |
| 2009/0043260 A1 | 2/2009 | Bierman |
| 2009/0254040 A1 | 10/2009 | Bierman et al. |
| 2009/0299294 A1 | 12/2009 | Pinkus |
| 2009/0306603 A1 | 12/2009 | Bierman et al. |
| 2010/0179482 A1 | 7/2010 | Wright et al. |
| 2010/0179483 A1 | 7/2010 | Wright et al. |
| 2011/0178467 A1 | 7/2011 | Bierman et al. |
| 2011/0264050 A1 | 10/2011 | Henry et al. |
| 2011/0282291 A1 | 11/2011 | Ciccone |
| 2012/0041378 A1 | 2/2012 | Bierman |
| 2013/0079723 A1 | 3/2013 | Andino et al. |
| 2015/0088076 A1 | 3/2015 | Andino |
| 2017/0296788 A1 | 10/2017 | Andino et al. |

FOREIGN PATENT DOCUMENTS

| | | |
|---|---|---|
| DE | 2341297 A1 | 4/1975 |
| EP | 0064284 A2 | 11/1982 |
| EP | 0114677 A2 | 8/1984 |
| EP | 0169704 A1 | 1/1986 |
| EP | 0247590 A2 | 12/1987 |
| EP | 0263789 A1 | 4/1988 |
| EP | 0356683 A1 | 3/1990 |
| EP | 0367549 A2 | 5/1990 |
| EP | 0720836 A2 | 7/1996 |
| EP | 0931560 A1 | 7/1999 |

(56) References Cited

FOREIGN PATENT DOCUMENTS

| | | | |
|---|---|---|---|
| FR | 2381529 | A1 | 9/1978 |
| FR | 2598625 | A1 | 11/1987 |
| GB | 2063679 | A | 6/1981 |
| GB | 2086466 | A | 5/1982 |
| GB | 2178811 | A | 2/1987 |
| GB | 2211417 | A | 7/1989 |
| GB | 2472268 | A | 2/2011 |
| JP | 52-004691 | B | 2/1977 |
| JP | 62201159 | A | 9/1987 |
| JP | 63501477 | | 6/1988 |
| JP | 01308572 | | 12/1989 |
| JP | 1995-028563 | | 5/1995 |
| WO | 8001458 | A1 | 7/1980 |
| WO | 90/04991 | A1 | 5/1990 |
| WO | 9005559 | A1 | 5/1990 |
| WO | 9116939 | A1 | 11/1991 |
| WO | 9203070 | A1 | 3/1992 |
| WO | 9203923 | A1 | 3/1992 |
| WO | 9219309 | A1 | 11/1992 |
| WO | 9219314 | A1 | 11/1992 |
| WO | 9412231 | A1 | 6/1994 |
| WO | 9421319 | A1 | 9/1994 |
| WO | 9610435 | A1 | 4/1996 |
| WO | 9715337 | A1 | 5/1997 |
| WO | 9715342 | A1 | 5/1997 |
| WO | 9853872 | A1 | 12/1998 |
| WO | 9955409 | A1 | 11/1999 |
| WO | 2004016309 | A2 | 2/2004 |
| WO | 2005105194 | A1 | 11/2005 |
| WO | 2007117655 | A2 | 10/2007 |
| WO | 2008051810 | A2 | 5/2008 |
| WO | 2008151047 | A1 | 12/2008 |
| WO | 2009055739 | A1 | 4/2009 |
| WO | 2010102153 | A1 | 9/2010 |

OTHER PUBLICATIONS

ARROW® "Snap-Lock" Catheter/Syringe Adapter, 1 page, K-05500-103A (Jan. 1990).

CA 2775570 filed Mar. 27, 2012 Office Action dated Aug. 8, 2016.
CA 2776239 filed Mar. 29, 2012 Office Action dated Jul. 15, 2016.
CA 2776239 filed Mar. 29, 2012 Office Action dated May 1, 2017.
PCT/US12/34533 filed Apr. 20, 2012 International Search Report and Written Opinion dated Aug. 10, 2012.
PCT/US2010/051659 filed Jun. 10, 2010 International Search Report dated Dec. 3, 2010.
PCT/US2010/051706 filed Jun. 10, 2010 International Search Report and Written Opinion dated Dec. 2, 2010.
Search Result, Percufix® Catheter Cuff Kit, downloaded from the Internet on Aug. 15, 2001.
U.S. Appl. No. 12/175,351, filed Jul. 17, 2008 Decision on Appeal dated Nov. 2, 2017.
U.S. Appl. No. 12/175,351, filed Jul. 17, 2008 Notice of Allowance dated Dec. 15, 2017.
U.S. Appl. No. 13/498,117, filed Dec. 10, 2012 Final Office Action dated Nov. 2, 2015.
U.S. Appl. No. 13/498,117, filed Dec. 10, 2012 Non-Final Office Action dated Jul. 22, 2015.
U.S. Appl. No. 13/498,118, filed Jul. 2, 2012 Final Office Action dated Nov. 2, 2016.
U.S. Appl. No. 13/498,118, filed Jul. 2, 2012 Final Office Action dated Oct. 22, 2015.
U.S. Appl. No. 13/498,118, filed Jul. 2, 2012 Notice of Allowance dated Feb. 16, 2017.
U.S. Appl. No. 14/557,904, filed Dec. 2, 2014 Non-Final Office Action dated Sep. 19, 2016.
U.S. Appl. No. 15/637,909, filed Jun. 29, 2017 Advisory Action dated Mar. 19, 2019.
U.S. Appl. No. 15/637,909, filed Jun. 29, 2017 Final Office Action dated Jan. 11, 2019.
U.S. Appl. No. 15/637,909, filed Jun. 29, 2017 Non-Final Office Action dated Sep. 25, 2018.
U.S. Appl. No. 15/637,909, filed Jun. 29, 2017 Notice of Allowance dated Jun. 5, 2019.

* cited by examiner

STABILIZING DEVICE HAVING A SNAP CLAMP

CROSS-REFERENCE TO RELATED APPLICATIONS

This application is a continuation of U.S. patent application Ser. No. 15/637,909, filed Jun. 29, 2017, now U.S. Pat. No. 10,426,928, which is a continuation of U.S. patent application Ser. No. 13/498,118, filed Jul. 2, 2012, now U.S. Pat. No. 9,694,130, which is a U.S. National Stage of International Patent Application No. PCT/US2010/051706, filed Oct. 6, 2010 and titled "STABILIZING DEVICE HAVING A SNAP CLAIM," which claims priority under 35 U.S.C. § 119(e) to U.S. Provisional Application No. 61/249,212, filed Oct. 6, 2009 and titled "STABILIZING DEVICE HAVING A SNAP CLAIM," each of which is incorporated by reference in its entirety into this application.

BACKGROUND

1. Field of the Invention

The present invention relates generally to techniques, systems, and devices for securing a catheter or other medical article to a patient.

2. Description of the Related Art

Medical patients are often in need of repetitious administering of fluids or medications, or repetitious draining of fluids. It is very common in the medical industry to utilize medical tubing to provide various liquids or solutions to a patient. For example, medical tubing such as a catheter is often used to introduce fluids and medications directly into the patient or to withdraw fluids from the patient. In many cases, the catheter remains in place for many days. In some instances, a catheter may be attached to a patient for an even lengthier period of time, and may require minimal movement for proper functioning.

It is often advantageous to restrict the movement of the catheter. A moving catheter may cause discomfort to the patient, restrict the administering of fluids or medications or the draining of fluids, cause infection, or become dislodged from the patient unintentionally. In order to keep the catheter or other medical tubing properly positioned for the duration of treatment, the catheter or medical tubing can be secured to the patient in a variety of ways. Most commonly, the medical provider may attempt to restrict movement of the catheter by securing the distal end of the catheter, or a portion of a medical device connected to the catheter such as a connector fitting, to the patient using tape. Medical providers commonly place long pieces of tape across the distal end of the catheter, often in a crisscross pattern, to secure the catheter distal end to the patient. This securement is intended to inhibit disconnection between the catheter and the patient or between the catheter and another medical article, such as a drainage tube, as well as to prevent the catheter from catching on other objects, such as on a bed rail.

Securing a catheter with tape upon the patient, however, has certain drawbacks. For example, taped connections often collect contaminants and dirt. This potentially can lead to infection of the patient, particularly at an insertion site where the catheter is inserted into the patient. Normal protocol therefore requires periodic tape changes in order to inhibit germ growth.

Periodic tape changes may also be necessary when replacing or repositioning the medical article. The frequent, often daily, removal and reapplication of adhesive tape to the skin of the patient can excoriate the skin. Such repeated applications of tape over the catheter or medical tubing can additionally lead to the buildup of adhesive residue on the outer surface of the catheter or medical tubing. This residue can result in contaminants adhering to the catheter itself, increasing the likelihood of infection of the insertion site. This residue can also make the catheter or medical tubing stickier and more difficult to handle for medical providers.

To add to the above problems, valuable time is spent applying and reapplying the tape to secure the catheter. And medical providers often remove their gloves when taping because most find the taping procedure difficult and cumbersome when wearing gloves, especially when the catheter has become sticky from repeated tape applications. Not only does this further lengthen the procedure, but it also may subject the medical provider to possible infection and increase the risk of needle-stick.

Furthermore, tape often fails to limit catheter motion and, therefore, contributes to motion related complications like phlebitis, infiltration and catheter migration. Also, the removal of taped dressings can itself cause undesired motion of the catheter upon the patient. Thus, a patient is subjected to a risk each time that the catheter is intentionally or unintentionally moved or adjusted.

SUMMARY OF THE INVENTION

The devices and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Embodiments," one will understand how the features of this invention provide several advantages over other securement devices.

One aspect of the present invention includes a retainer for securing a medical article to a patient. The retainer includes a base, and a plurality of walls supported by the base and forming a channel therebetween. At least one of the plurality of walls is movable towards another one of the plurality of walls and between an open and closed position. The retainer further includes an actuation surface configured to move the moveable wall from at least the open position to the closed position when pressed in a direction towards the base, and a support having a first end and a second end. The first end is fixed to the base and the second end is attached to the at least one moveable wall via a flexible coupling. In some embodiments, the flexible coupling is spaced in a lateral direction from the first end.

Another aspect of the present invention includes a stabilization system having a first configuration for accepting a medical article and a second configuration for securing a medical article. The stabilization device includes an anchor pad having a first surface and a retainer supported by the anchor pad. At least a portion of the first surface is covered by an adhesive for attachment to a patient's skin. The retainer includes a base and first and second walls supported by the base. At least one of the first and second walls is movable in an outward direction with respect to the other wall. Each wall comprises an inner surface having an arcuate shape. The retainer further includes an actuation surface disposed between the first and second walls, and at least a first support spacing the actuation surface from the base at least when in the first configuration. The actuation surface is configured to cause the walls to encircle an outer circumference of at least a portion of the medical article when the medical article is pressed against the actuation surface.

Yet another aspect of the present invention includes a retainer having an open configuration and a closed configuration. The retainer includes a pair of receiving surfaces defining a receiving space therebetween for receiving a medical article when the retainer is in the open configuration. The receiving surfaces contact at least a portion of the medical article when the retainer is in the closed configuration. The retainer further includes a coupling connected to at least one of the receiving surfaces so as to permit movement of the at least one receiving surface in a direction toward the other receiving surface, and at least one actuation surface. The at least one actuation surface is coupled to the at least one receiving surface and configured for movement in at least a generally transverse direction. Pressing the medical article against the actuation surface when the retainer is in the open configuration moves the at least one receiving surface in the direction toward the other receiving surface.

BRIEF DESCRIPTION OF THE DRAWINGS

The above mentioned and other features of the invention will now be described with reference to the drawings of several embodiments of the present stabilization system. The illustrated embodiments of the stabilization system are intended to illustrate, but not to limit the invention. The drawings contain the following figures.

DETAILED DESCRIPTION OF CERTAIN EMBODIMENTS

The following description and examples illustrate preferred embodiments of the present stabilization system disclosed in the context of use with an exemplary connector fitting. More specifically, the embodiments relate to a stabilization system and related techniques that stabilize a medical article in position upon a patient. The embodiments of the stabilization system are illustrated with a connector fitting having a male luer-lock connection fitting. The principles of the present invention, however, are not limited to fittings such as those shown. It will be understood by those of skill in the art in view of the present disclosure that the securement system described can be used with other types of medical articles, including, but not limited to catheters and catheter hubs of various design, either with or without connectors, such as central venous catheters, peripherally inserted central catheters, hemodialysis catheters, and Foley catheters, as well as other designs of catheter hubs and catheter adaptors. Other medical articles may include surgical drainage tubes, feeding tubes, chest tubes, nasogastric tubes, rectal drains, external ventricular drains, any other sort of fluid supply or medical lines, and scopes, as well as electrical wires or cables connected to external or implanted electronic devices or sensors. The medical articles can be a single medical article or a combination of medical articles.

One skilled in the art may also find additional applications for the devices and systems disclosed herein. Accordingly, the illustration and description of the stabilization system in connection with a connector fitting is merely exemplary of one possible application of the stabilization system and technique disclosed. For ease of description, the term fitting or connector fitting is used herein to generically refer to the above listed medical articles, for example but without limitation, and should not be construed in a limited manner.

The securement system described herein is especially adapted to arrest at least transverse movement of a connector fitting, as well as hold the fitting against the patient. The securement system accomplishes this without meaningfully impairing (i.e., substantially occluding) fluid flow through the fitting or an attached medical tube. As described below, retention mechanisms to accomplish this include, among others, a moveable channel having a snapping latch mechanism to clamp the fitting in place.

The stabilization system releasably engages the connector fitting. This allows the fitting to be disconnected from the stabilization system, and from the patient, for any of a variety of known purposes. For instance, the medical provider may want to remove the fitting from the anchor pad to ease disconnection of a medical article from the fitting or to clean the patient. The disengagement of the fitting from the stabilization system, however, can be accomplished without removing the anchor pad from the patient. Thus, the medical provider may move the fitting without irritating the skin of the patient.

In some embodiments, components of the stabilization system can be reused. It is not limited to use for only one connector fitting, but can be used multiple times for the same fitting or for different fittings. After disengagement of the fitting, the anchor pad or strap is ready for re-engaging with the same or a different fitting. A detailed description of embodiments of a securement system, and its associated method of use, now follows.

Figure 1:
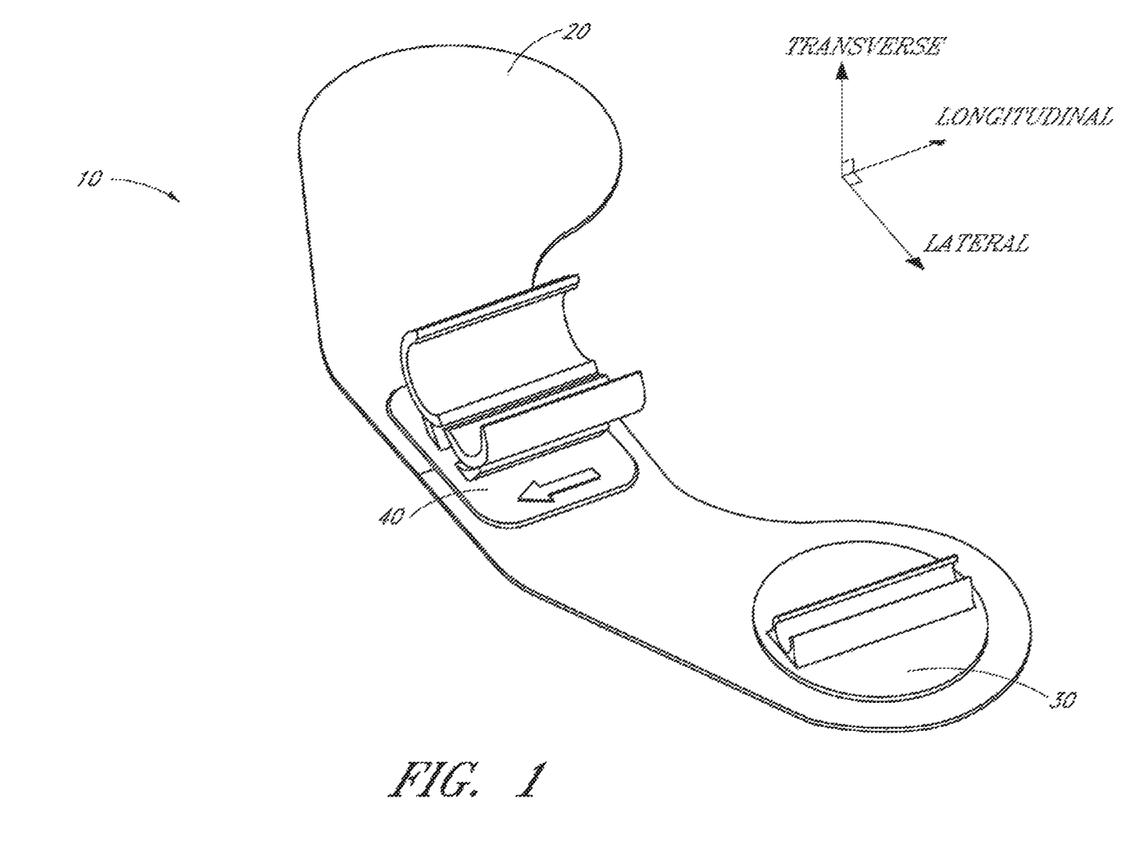
FIG. 1 is a perspective view of a stabilization system in accordance with a preferred embodiment of the present invention and shows a retainer and a tube clip being supported by an anchor pad.

With reference now to FIG. 1, an embodiment of a stabilization system 10 includes an anchor pad 20 and a retainer 40 supported by the anchor pad 20. The anchor pad 20 is configured to be secured to a patient's skin. The stabilization system may further include a tube clip 30. The retainer 40 is configured to engage a medical article, as will be described in additional detail below.

To assist in the description of the components of embodiments of the anchoring system, the following coordinate terms are used, consistent with the coordinate axes illustrated in FIG. 1. A "longitudinal axis" is generally parallel to a channel formed by the retainer 40. A "lateral axis" is normal to the longitudinal axis and is generally parallel to the plane of the anchor pad 20. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The terms "proximal" and "distal" are used in reference to the center of the patient's body.

Figure 2:
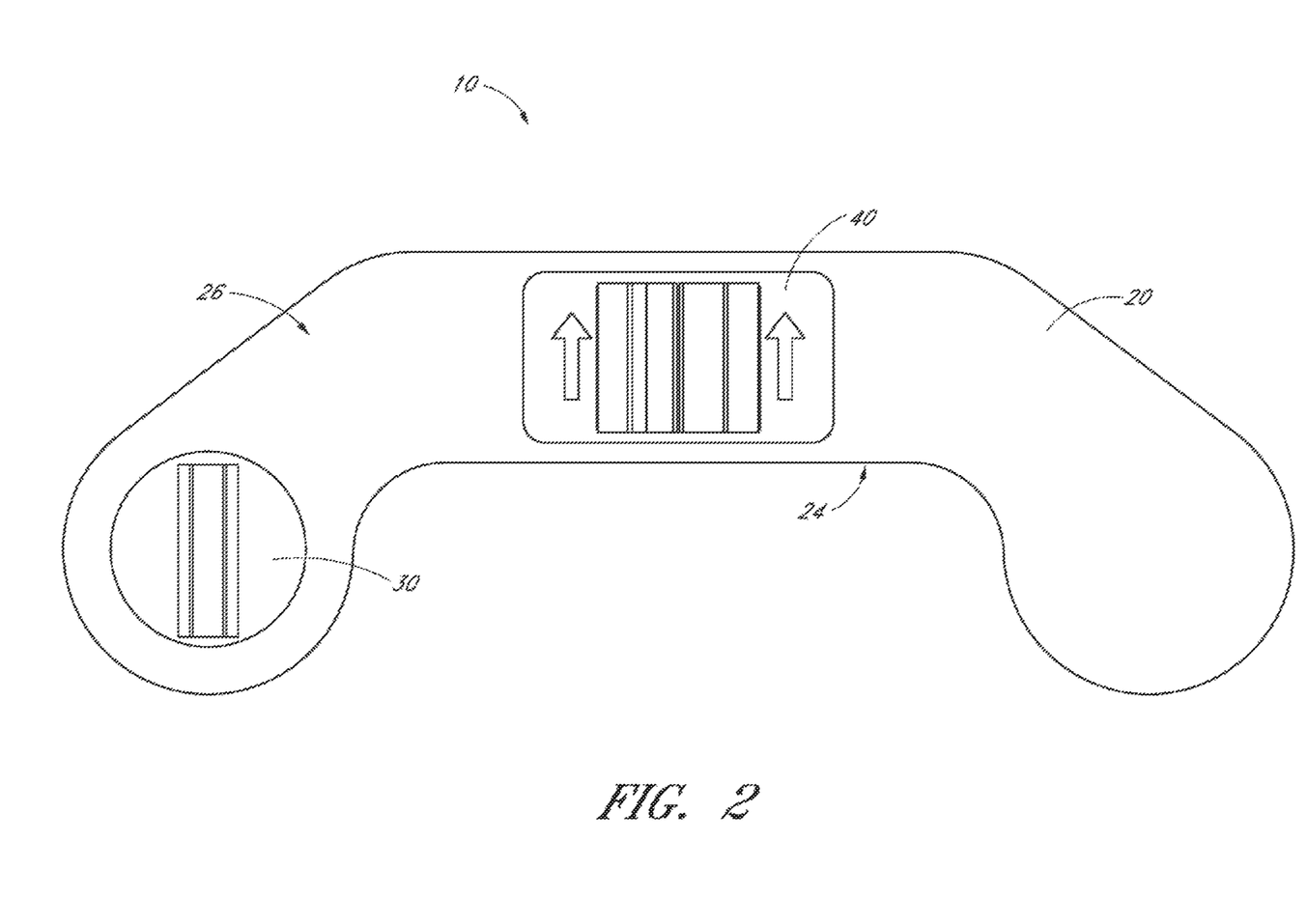
FIG. 2 is a top view of the stabilization system of FIG. 1.

As can be seen in a top view of the stabilization system 10, as shown in FIG. 2, the anchor pad 20 is generally crescent shaped and has rounded ends. In the illustrated embodiment, the anchor pad 20 is configured for placement on a distal surface of a patient's hand. The anchor pad 20, however, may be larger or smaller, and may be shaped for placement on a different area of the patient's body. The anchor pad 20 may be any size or shape that allows attachment of the anchor pad 20 to a patient's skin and that is configured to support at least the retainer 40. In the illustrated embodiment, the anchor pad 20 is also configured to support the tube clip 30. In other embodiments, the tube clip 30 is omitted. In some embodiments, the tube clip 30 is supported by a separate, auxiliary anchor pad.

The anchor pad 20 has a lower adhesive surface 24 which may adhere to the skin of a patient and an upper layer 26. The upper layer 26 is configured to support at least the retainer 40, as described above. In combination, the lower adhesive surface 24, upper layer 26, and possibly one or more intermediate layers may comprise a laminate structure. A suitable laminate that comprises a foam or woven material with an adhesive layer is available commercially from Avery Dennison of Painsville, Ohio. The anchor pad 20 may be configured as a flexible structure configured to conform to the surface of a patient's skin.

The lower adhesive surface 24 or layer may be a medical-grade adhesive and can be either diaphoretic or non-diaphoretic, depending upon the particular application. The lower adhesive surface may have additional types of medical adhesives laminated thereto. The adhesive surface may be a solid layer or may be configured as an intermittent layer such as in a pattern of spots or strips.

The lower adhesive surface 24 can be applied to the anchor pad 20 during manufacture, and may be further covered with a release liner (not shown), described below. Alternatively, it is possible to apply a double-sided adhesive tape to the upper layer 26 before application.

The upper layer 26 may comprise a foam (e.g., closed-cell polyethylene foam) or woven material (e.g., tricot) layer. A surface of the foam or woven material layer constitutes the upper layer 26 of the anchor pad 20. In the alternative, the upper layer 26 may comprise an upper paper or other nonwoven cloth layer, and an inner foam layer may be placed between the upper layer 26 and lower adhesive surface 24.

A removable release liner may cover the lower adhesive surface 24 before use. The release liner may resist tearing and be divided into a plurality of pieces to assist removal of the release liner and ease attachment of the anchor pad 20 to a patient's skin. The release liner may be divided into two adjacent pieces. The liner may be made of a paper, plastic, polyester, or similar material. For example, the release liner may comprise a material made of polycoated, siliconized paper, or another suitable material such as high density polyethylene, polypropylene, polyolefin, or silicon coated paper.

Figure 3:
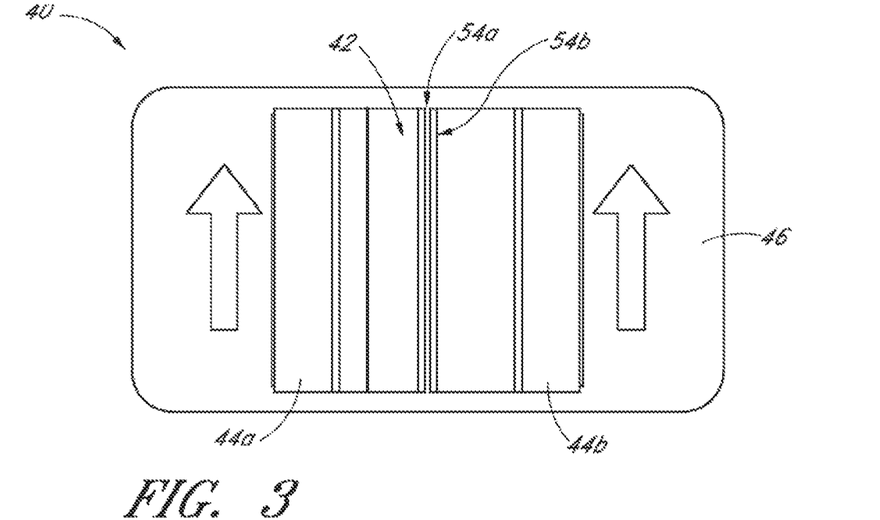
FIG. 3 is a top view of the retainer from FIG. 1.

FIG. 3 illustrates a top view of the retainer 40. In the illustrated embodiment, retainer 40 includes arrows that point towards an insertion site where a catheter or other medical device stabilized in connection with the stabilization system 10 is inserted into the body of a patient. In other embodiments, the arrows are omitted.

Figure 4:
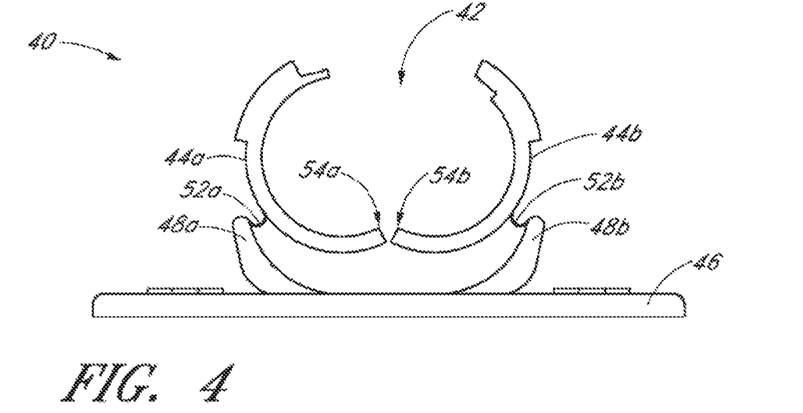
FIG. 4 is a front view of the retainer from FIG. 3 and shows the retainer in an open configuration.

FIG. 4 illustrates a side view of the retainer 40 in an open configuration. The retainer 40 includes a hinged channel 42 having movable walls 44a and 44b. The walls 44a, 44b each include an arcuate inner surface that functions as a receiving surface of the retainer 40. When in the open position, the walls 44a and 44b define a receiving space therebetween to accept a medical article. Desirably, the shape of the channel 42 conforms substantially to a cylindrical shape, thereby allowing the channel 42 to mate easily with a connector fitting, as described below. The arcuate surface of each wall 44a and 44b has a radius of curvature that generally matches the fitting. Each wall 44a and 44b extends through an arc length of generally 180 degrees such that together the walls 44a and 44b will surround the fitting. In other embodiments, the walls 44a and 44b have an arc length of less than 180 degrees. Although the channel 42 is illustrated as being substantially uniform in diameter, a diameter of the channel 42 may vary along the length of the channel. For example, the channel 42 may have a tapering configuration. In the illustrated embodiment, the walls 44a and 44b are formed separately from one another. In other embodiments, the walls 44a and 44b may be linked or formed as a unitary structure. For example, a terminal portion of each of the walls 44a and 44b (nearest the anchor pad) may be connected by a hinge, for example a living hinge.

The walls 44a and 44b are connected to a base 46 of the retainer 40 by supports 48a and 48b. Flexible couplings 52a and 52b allow the walls 44a and 44b, respectively, to pivot with respect to the supports 48a and 48b, respectively. In the illustrated embodiment, the couplings 52a and 52b are illustrated as thin lengths of material that form a living hinge area. The flexible couplings 52a and 52b may be configured to expand or stretch under stress. In other embodiments, one or more of the couplings comprise a different type of hinge or other mechanism that allows one or more of the walls 44a and 44b to pivot and/or slide with respect to the supports 48a and 48b, respectively. For example, a protrusion attached to an outer surface of one of the walls 44a or 44b may slide and pivot within a slot of the support 48a or 48b, respectively.

The walls 44a and 44b thus are movable relative to each other and to the base 46. Desirably, the flexible couplings 52a and 52b normally hold the walls 44a and 44b, respectively, in an open position, as illustrated in FIG. 4. In the open configuration, upper ends (distal of or remote from the base 46) of the walls 44a and 44b are spaced apart and may accept a medical article therebetween. As discussed above, the spacing of the walls 44a and 44b when in the open configuration therefore creates a receiving space. The flexible couplings 52a and 52b permit the walls 44a and 44b, respectively, to move toward each other into a closed position, as will be described below. In the illustrated embodiment, the retainer 40 is configured to accept the medical article from a location generally above the retainer 40. In other embodiments, the receiving space may be designed to accept a medical article from below at least a portion of the retainer, for example such that the retainer may be placed over a medical article and secured by pressing down on the retainer.

The retainer 40 includes actuation surfaces 54a and 54b. In the illustrated embodiments, the actuation mechanisms 54a and 54b are defined by lower ends of the walls 44a and 44b, respectively. In some embodiments, a single actuation surface may be formed by either of the actuation surfaces 54a and 54b, or by a hinged area where the walls 44a and 44b are connected. The actuation surfaces 54a and 54b are exposed when the retainer 40 is in the open position, as can be seen in the top view of the retainer 40 in FIG. 3. The actuation surfaces 54a and 54b are oriented and sized to have a slight upwardly orientation when the retainer 40 is in the open position, as seen in FIG. 4. In other embodiments, an actuation surface is attached to one or both lower ends of the walls 44a and 44b and extends above the lower ends into the channel 42 when the retainer 40 is in the open configuration. In this embodiment, the actuation surface may be configured to lie flat against or flush with the inner surface of the walls 44a and 44b when the retainer is in the closed configuration.

Figure 5:
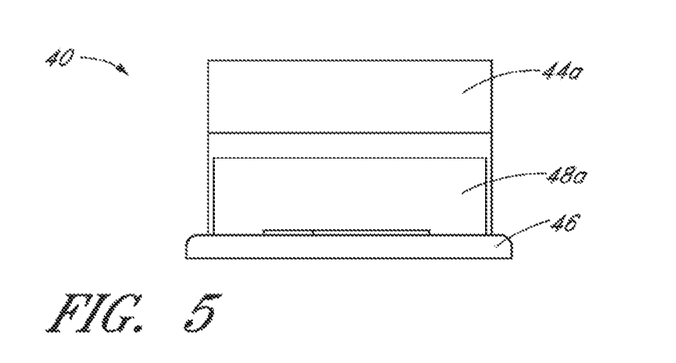
FIG. 5 is a side view of the retainer from FIG. 3.

As can be seen in a side view of the retainer 40, as illustrated in FIG. 5, the support 48a (and 48b, although not shown) is approximately as long in the longitudinal direction as the wall 44a (and the wall 44b). In other embodiments, one or more of the supports 48a and 48b may be shorter or longer in comparison to one or more of the walls 44a and 44b.

Figure 6:
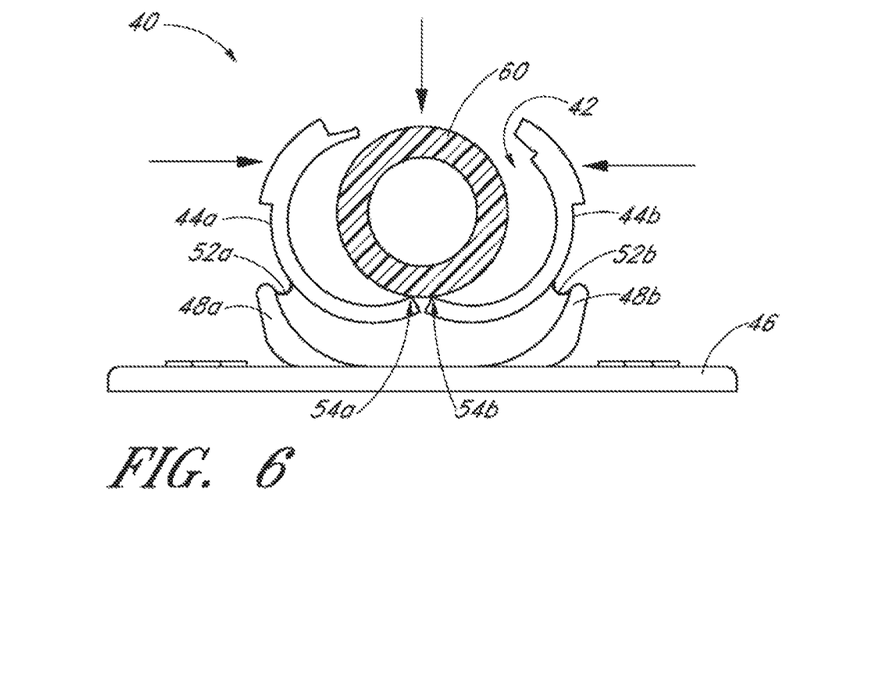
FIG. 6 is a front view similar to FIG. 4 except that a medical article is disposed in the retainer.

FIG. 6 illustrates a side view of the retainer 40 in combination with a medical article 60. In the open configuration, the retainer 40 is configured to accept the medical article 60 between the walls 44a and 44b. When the medical article 60 is pressed into the channel 42 such that the actuation surfaces 52a and 52b are contacted by the medical article 60, the actuation surfaces 52a and 52b may be pressed in a downward direction. For example, a medical provider may insert the medical article 60 into the channel 42 and press down on the medical article 60. Such action will cause the actuation surfaces 52a and 52b to move towards the base 46. This downward movement of the actuation surfaces 54a and 54b causes the walls 44a and 44b to move with respect to the supports 48a and 48b, respectively. Consequently, the flexible couplings 52a and 52b will flex and/or stretch, and the arcuate inner surfaces of the walls 44a and 44b will move toward the medical article 60.

Figure 7:
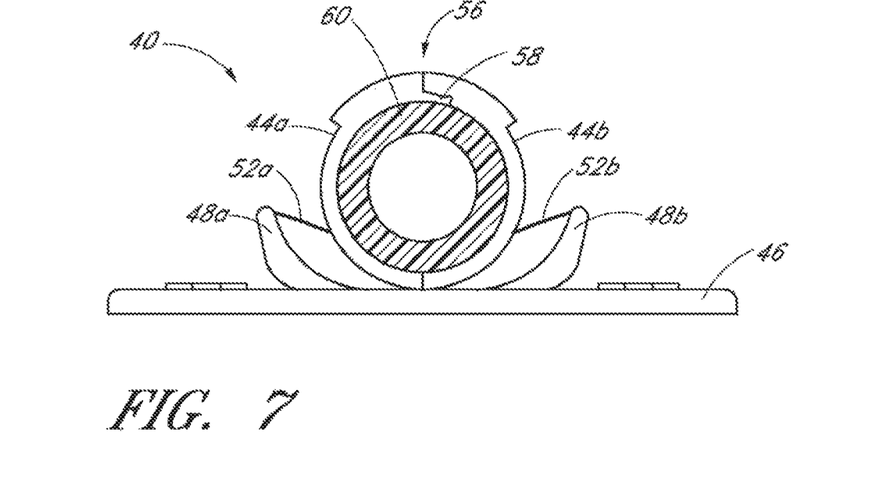
FIG. 7 is a front view of the retainer and medical article from FIG. 6, and shows the retainer in a closed configuration about the medical article.

If the medical article 60 is depressed far enough, the upper ends of the walls 44a and 44b will be pressed together, as seen in FIG. 7. This is the closed configuration. In this configuration, the shape and size of the channel 42 generally matches that of the retained section of the medical article 60. The channel 42 thus surrounds the circumference of a portion of the medical article 60. The walls 44a and 44b may be configured to press against the base 46, as shown in FIG. 7, when one or more of the flexible couplings 52a and 52b are in a fully actuated position. In this way, the base 46 may be configured to prevent further transverse motion of the walls 44a and 44b, which may reduce the likelihood of damaging the couplings 52a and 52b and may inhibit occlusion of or damage to the article 60.

In the illustrated embodiment, a protrusion 58 on the end of the wall 44a is configured to fit beneath a recess of the wall 44b. In this way, a latching mechanism is formed that will maintain the retainer 40 in the closed position. In some embodiments, the latching mechanism further comprises a lip to increase the security of the connection between the walls 44a and 44b. In other embodiments, a detent or series of detents and a matching cavity or series of cavities may be included to increase the security of the connection between the walls 44a and 44b. In some embodiments, the latching mechanism may be engaged by a medical provider by pushing down on a top surface 56 of the walls 44a and 44b after the retainer 40 is already in the closed position. This will serve to snap the latching mechanism in place, thereby clamping the retainer 40 about the medical article 60. The latching mechanism may comprise any number of devices or structures that are configured to hold the walls 44a and 44b in position about the medical article 60. Those of skill in the art will appreciate that the medical provider may therefore insert the medical article 60 into the retainer 40, and then close and latch the retainer 40 about the medical article 60, with one hand. In some embodiments, a frictional fit of the protrusion 58 and the recess are sufficient to hold the walls 44a and 44b in contact with the medical article 60, thereby circumscribing a portion of the medical article 60. For example, the retainer 40 may be temporarily maintained in the closed configuration due to the frictional fit such that a medical provider may break contact with the medical article 60 and the retainer 40 and thereafter depress the top 56 of the walls to engage the latching mechanism.

Portions of the retainer 40 may be formed as a unitary structure. For example, two or more of the base 46, walls 44a and 44b, supports 48a and 48b, and couplings 52a and 52b may be integrally formed to comprise a unitary retainer. For example, the couplings 52a and 52b may comprise the same material as other components of the retainer 40, but may be thinned to allow flexing and/or stretching of the couplings 52a and 52b. In some embodiments, the base 46 and supports 48a and 48b are integrally formed. This may be accomplished in any of a variety of ways well known to those skilled in the art. For example, these components can be injection molded in order to reduce fabrication costs. Of course, one or more components of the retainer 40 could be formed separately and then coupled together. For example, the walls 44a and 44b may be formed separately from the base 46 and supports 48a, 48b; these elements may then be connected together using appropriate coupling means or materials. In this way, the retainer 40 may be non-unitary.

Additionally, elements of the retainer 40 may have other forms or other orientations relative to one another than what is illustrated. The retainer 40, elements, or portions thereof may be formed by injection molding using polyethylene or polypropylene material. Other suitable materials may include, for example, but without limitation: plastics, polymers or composites such as polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. However, other materials may be utilized.

Figure 8:
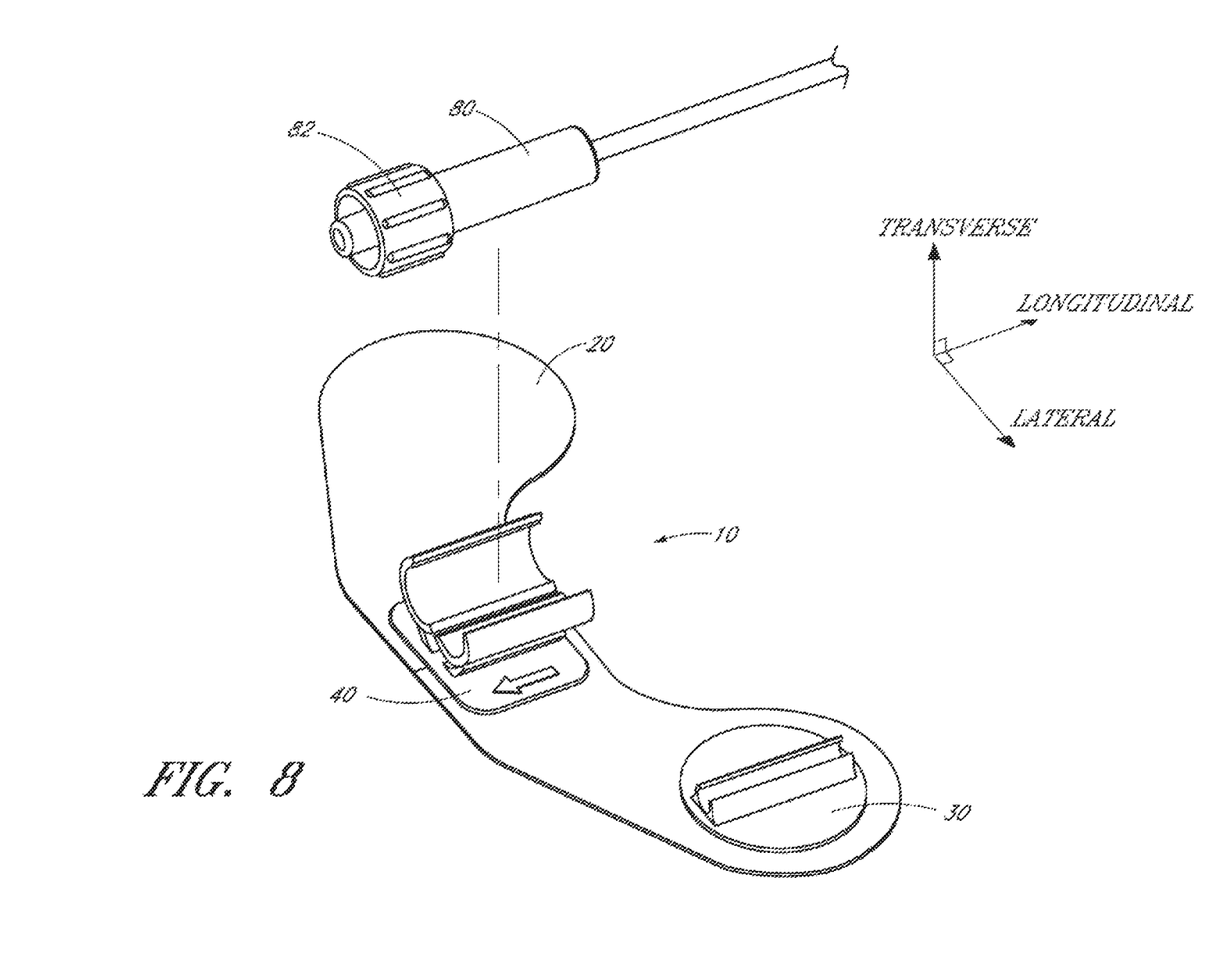
FIG. 8 is a perspective view of the stabilization system of FIG. 1, and shows a medical article being aligned above the stabilization system prior to insertion.

FIG. 8 shows a connector fitting 80 placed above the stabilization system 10. In the illustrated embodiment, the fitting 80 comprises a male luer-lock connector fitting. The fitting 80 may also comprise an annular collar 82 to ease insertion or removal of the luer-lock connector fitting. In some embodiments, the collar 82 is configured as a spin nut, and may include a threaded interior portion to increase securement of the fitting 80 to another medical article, for example a catheter or catheter hub.

Figure 9:
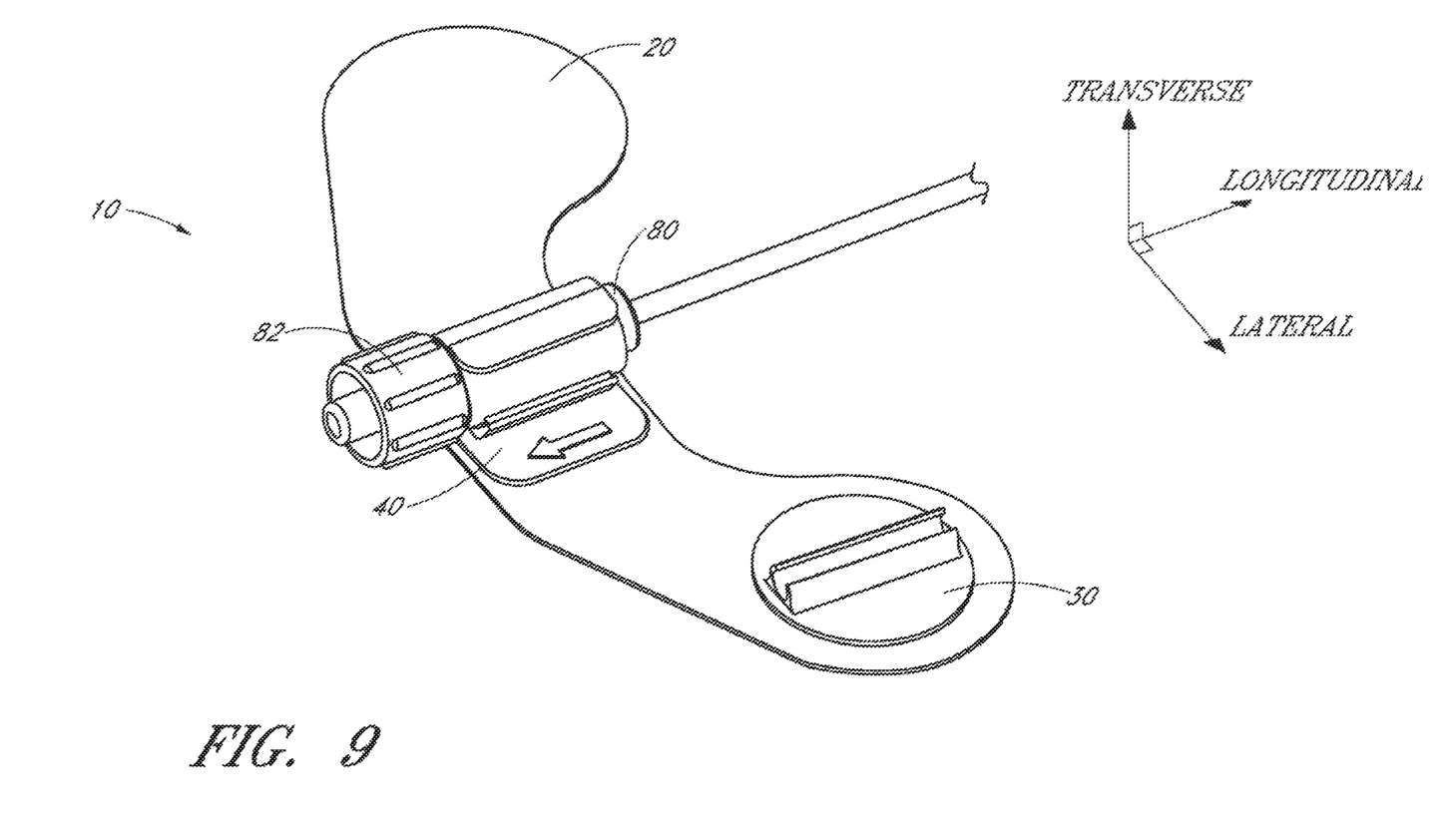
FIG. 9 is a perspective view of the stabilization system and medical article of FIG. 8, and shows the medical article secured within the stabilization system.

As described above with respect to the medical article 60 illustrated in FIG. 6, the fitting 80 may be lowered into the retainer 40. Pressing the fitting 80 into the retainer 40 will cause the retainer 40 to close about the fitting 80, as shown in FIG. 9. As described above, the channel 42 is configured to approximately match the size and shape of the fitting 80. In other embodiments, the channel 42 is configured to match or approximate other medical articles. Not only will the size and shape of the channel 42 decrease the likelihood of occluding a medical article, but securing the retainer 40 about a rigid fitting will also decrease the likelihood of occlusion. When stabilized as shown in FIG. 9, the spin nut of the fitting 80 may abut against the retainer 40, and will thereby be inhibited from moving in at least one longitudinal direction. In some embodiments, a shape of a proximal end of one or both of the walls 44a and 44b may be matched to a shape of a distal surface of the annular collar 82 or may be configured to interengage with the distal surface of the annular collar 82. Thus, the retainer 40 may be configured with an abutment surface. Further, the shape of the channel 42 will inhibit the fitting 80 from moving in lateral or transverse directions.

An adhesive may further be placed within the channel 42 so as to contact an outer surface of the fitting 80. In some embodiments, compressible glue and/or at least one glue dot is disposed on a surface of the channel 42. In some embodiments, a different compressible material and/or an elastomeric material is disposed on a surface of the channel 42. Such structures when in contact with the medical article may apply a force towards a center of the channel 42 when the retainer 40 is closed about a medical article, and may increase the reliability of the securement of the medical article or may be configured to accommodate medical articles of different widths or diameters, or otherwise varying in size.

Figure 10:
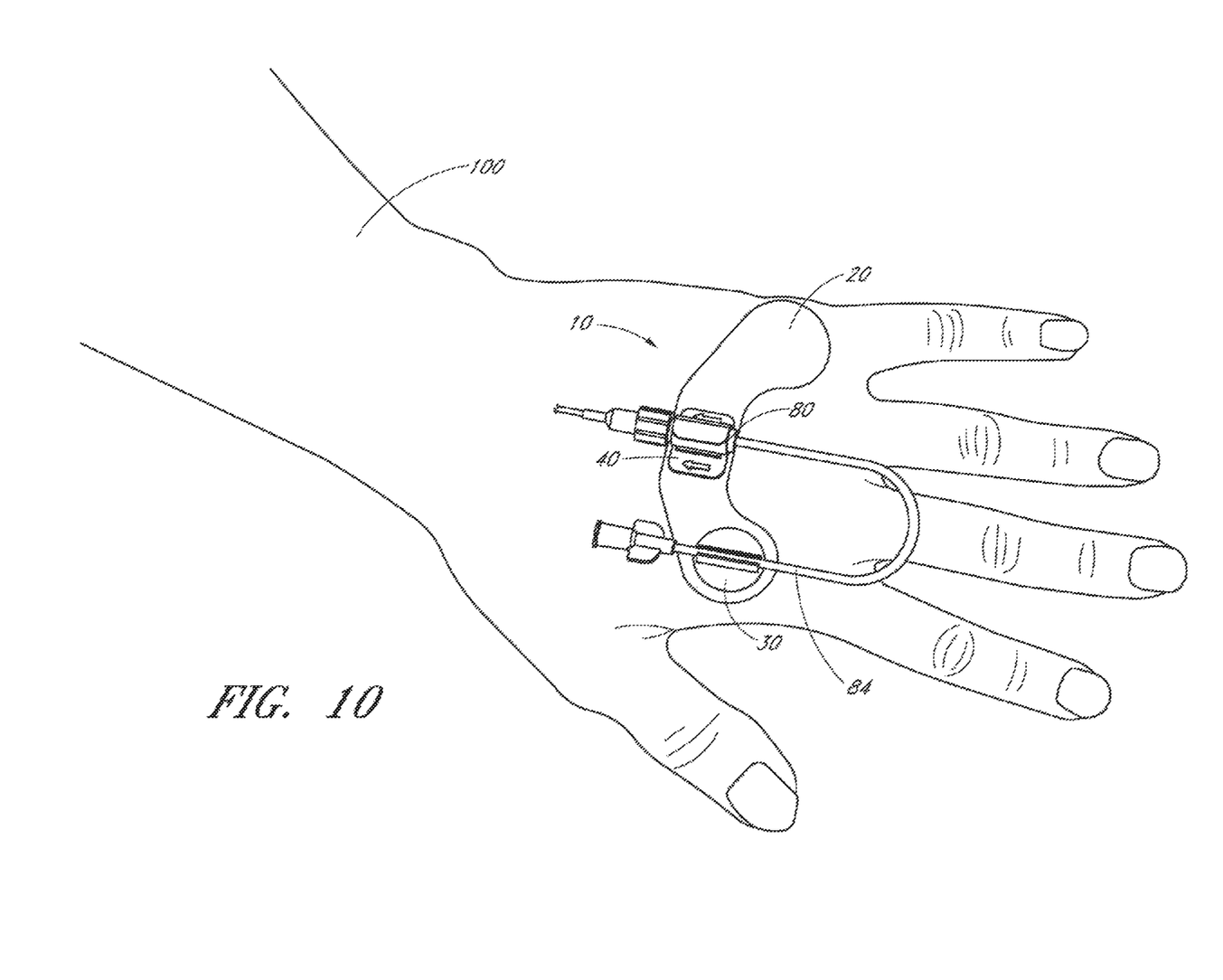
FIG. 10 is a top view of the stabilization system of FIG. 1 securing a medical article to a patient.

FIG. 10 shows the stabilization system 10 and the fitting 80 attached to a patient 100. In the illustrated embodiment, the fitting 80 is snapped into the retainer 40, and the anchor pad 20 is attached to a distal surface of the hand of the patient 100. In addition, the fitting 80 is shown as being connected to a catheter hub having a cannula and a female luer-lock connector fitting, which cannula is inserted into the patient's skin. In this way, the fitting 80 will be stabilized on the patient 100, and unintentional movement or withdrawal of the cannula will be inhibited.

In the configuration illustrated in FIG. 10, the fitting 80 is further stabilized by placing a portion of a medical tube 84, which is connected to the fitting 80, into the tube clip 30. As can be seen in FIG. 10, the clip 30 defines a channel having a generally circular cross-sectional configuration truncated to form an opening. The diameter of the channel is desirably slightly less than that of the medical line 84 so as to ensure a secure interconnection. The channel receives a portion of the medical line 84 through the opening upon application of gentle pressure or by pulling the line 84 across and through the opening of the tube clip 30. The clip 30 thereafter partially surrounds a portion of the line 84. The sides of the channel may be angled in relation to themselves or in relation to each other to accommodate a different medical line or other medical article.

The upper edge of the channel of the tube clip 30 may include tapered ends at the proximal and distal ends of the clip 30. Each tapered end may form a smooth transition between the side edge of the channel and the upper edge, and may taper in lateral width from the side edge toward the center of the tube clip 30. The tapered ends help guide the medical line 84 into the channel when a medical provider pulls the tube across the clip 30. Thus, the medical provider does not have to pinch the line 84 to insert it into the clip 30. Also, the medical provider's gloves do not get stuck in the clip 30 when inserting the line 84, as is typically the case where the medical provider is required to pinch the line 84 to insert it into the clip 30.

In some embodiments, the fitting 80 is released from the retainer 40 by pressing an outer surface of the walls 44a, 44b towards each other. This squeezing motion may unclasp or unsnap the latch, allowing the walls 44a, 44b to separate from each other. For example, pressure created in the latching mechanism when the walls 44a, 44b are pressed together may cause a lip, protrusion, or detent of the latching mechanism to become dislodged from a recess or cavity of the latching mechanism. In some embodiments, the couplings 52a, 52b are configured to bias the walls 44a, 44b into an open configuration, and the walls 44a, 44b will naturally open to expose the fitting 80 when the latching mechanism is unclasped.

In some embodiments, the arcuate shape of the inner surface of the walls 44a, 44b will inhibit the retainer 40 from occluding a medical article even when the walls 44a, 44b are squeezed together. Further, when a medical article such as the connector fitting 80 having a rigid portion is utilized within the retainer 40, occlusion of the medical article is further inhibited. Of course, those of skill in the art will appreciate other ways and methods that may be used to open the retainer 40 and/or remove a medical article from the retainer 40. In some embodiments, the retainer 40 is configured to lock around the medical article permanently or semi-permanently. In such configuration, the medical article cannot be easily removed from the retainer 40, and a medical provider may remove the stabilization system 10 and medical article from the patient as a unit. The stabilization system 10 and the medical article may then be conveniently disposed of.

It is to be noted that the figures provided herein are not drawn to any particular proportion or scale, and that many variations can be made to the illustrated embodiments. Those of skill in the art will recognize that the disclosed aspects and features shown herein are not limited to any particular embodiment of a stabilization system, and stabilization systems that include one or more of the features herein described can be designed for use with a variety of medical articles.

The various embodiments of the stabilization systems described above in accordance with the present invention thus provide a means to releasably secure a connector fitting to a patient. The fitting can be held within a snapping clamp that can be operated by merely pressing down on the fitting and/or stabilization device. In some instances, a medical provider may do this with one hand, and in some embodiments just one finger.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. In addition to the variations described herein, other known equivalents for each feature can be mixed and matched by one of ordinary skill in this art to construct stabilization systems and techniques in accordance with principles of the present invention.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but by a fair reading of the claims that follow.

What is claimed is:

1. A method of securing a medical article to a patient, comprising:
   obtaining a retainer, the retainer comprising:
      an anchor pad;

a base;

a first wall extending from a first latching end to a first actuator end; and a second wall extending from a second latching end to a second actuator end, the first wall and the second wall moving between an open configuration for receiving the medical article, and a closed configuration for securing the medical article, the first wall and the second wall co-operating to define a channel extending along a longitudinal axis in the closed configuration;

securing the anchor pad to a skin surface of the patient;

urging the medical article transversely to contact and move one of the first actuator end and the second acutator end parallel to a transverse axis;

transitioning the first wall and the second wall from the open configuration to the closed configuration; and releasably securing the first latching end to the second latching end.

2. The method according to claim 1, wherein the first actuator end and the second acutator end are spaced away from the base in the open configuration and contact the base in the closed configuration.

3. The method according to claim 1, wherein the retainer further comprises:

a first support fixed to the base;

a second support fixed to the base;

a first flexible coupling connecting the first support to the first wall; and a second flexible coupling connecting the second support to the second wall.

4. The method according to claim 3, wherein the first flexible coupling and the second flexible coupling transition from a relaxed condition in the open configuration to a stretched condition in the closed configuration.

5. The method according to claim 3, wherein the first flexible coupling connects to the first wall at a position between the first latching end and the first actuator end.

6. The method according to claim 3, wherein the second flexible coupling connects to the second wall at a position between the second latching end and the second actuator end.

7. The method according to claim 1, wherein each of the first wall and the second wall comprises an inner surface having an arcuate shape.

8. The method according to claim 1, wherein the channel has a tapered configuration.

9. The method according to claim 1, wherein releasably securing the first latching end to the second latching end includes engaging a protrusion disposed on the first latching end within a recess disposed on the second latching end.

10. The method according to claim 1, wherein securing the anchor pad includes adhering an adhesive layer disposed on a lower surface of the anchor pad to the skin surface of the patient.

11. A method of releasably securing a medical device to a patient, comprising:

obtaining a retainer, the retainer comprising:

an anchor pad configured for securing the retainer to a skin surface of the patient;

a first wall extending from a first contacting end to a first securing end; and a second wall extending from a second contacting end to a second securing end;

urging the medical device toward the skin surface of the patient to move the first contacting end and the second contacting end perpendicular to the skin surface of the patient;

moving the first wall and the second wall from an open configuration to a closed configuration;

latching the first securing end to the second securing end to secure the medical device to the patient;

unlatching the first securing end from the second securing end;

transitioning the first wall and the second wall from the closed configuration to the open configuration; and ejecting the medical device from the retainer.

12. The method according to claim 11, wherein the retainer further comprises:

a base;

a first support extending from the base;

a second support extending from the base;

a first flexible coupling connecting the first support to the first wall;

a second flexible coupling connecting the second support to the second wall;

the first flexible coupling and the second flexible coupling transitioning from a relaxed condition in the open configuration to a stretched condition in the closed configuration.

13. The method according to claim 11, wherein the first wall and the second wall each define an arcuate shape and a channel in the closed configuration.

14. The method according to claim 11, wherein the first wall and the second wall define a tapered channel in the closed configuration.

15. The method according to claim 14, wherein the tapered channel defines a smooth transition reducing in lateral width from a first longitudinal end to a second longitudinal end.

* * * * *